(12) United States Patent
Hörnig

(10) Patent No.: US 7,404,673 B2
(45) Date of Patent: Jul. 29, 2008

(54) METHOD FOR GENERATING A GAIN-CORRECTED X-RAY IMAGE

(75) Inventor: Mathias Hörnig, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 91 days.

(21) Appl. No.: 11/404,028

(22) Filed: Apr. 13, 2006

(65) Prior Publication Data
US 2006/0233305 A1 Oct. 19, 2006

(30) Foreign Application Priority Data
Apr. 15, 2005 (DE) .................. 10 2005 017 491

(51) Int. Cl.
*G01D 18/00* (2006.01)
*H05G 1/64* (2006.01)

(52) U.S. Cl. ............... 378/207; 378/22; 378/98.7

(58) Field of Classification Search ............ 378/22, 378/98.7, 207
See application file for complete search history.

(56) References Cited

U.S. PATENT DOCUMENTS

| 4,398,302 | A | * | 8/1983 | Pfeiler ............... 378/146 |
| 4,763,345 | A | * | 8/1988 | Barbaric et al. ........ 378/146 |
| 5,278,887 | A | * | 1/1994 | Chiu et al. ............ 378/156 |
| 5,530,238 | A | * | 6/1996 | Meulenbrugge et al. . 250/208.1 |
| 5,923,722 | A | * | 7/1999 | Schulz ............... 378/98.8 |
| 6,067,342 | A | * | 5/2000 | Gordon ............... 378/19 |
| 6,118,846 | A | * | 9/2000 | Liu .................. 378/62 |
| 6,196,715 | B1 | * | 3/2001 | Nambu et al. .......... 378/197 |
| 6,246,746 | B1 | * | 6/2001 | Conrads et al. ........ 378/98.7 |
| 6,632,020 | B2 | * | 10/2003 | Kaufhold et al. ........ 378/207 |
| 6,643,352 | B2 | * | 11/2003 | Oikawa ............... 378/21 |
| 6,707,878 | B2 | * | 3/2004 | Claus et al. .......... 378/22 |
| 6,850,589 | B2 | * | 2/2005 | Heumann et al. ........ 378/19 |
| 6,851,851 | B2 | * | 2/2005 | Smith et al. .......... 378/189 |
| 6,854,885 | B2 | * | 2/2005 | Wischmann et al. ...... 378/207 |
| 6,890,098 | B2 | * | 5/2005 | Rosner et al. ......... 378/196 |
| 6,914,958 | B2 | * | 7/2005 | Ganin ................ 378/26 |
| 6,973,160 | B2 | * | 12/2005 | Matsumoto ............ 378/22 |
| 6,980,624 | B2 | * | 12/2005 | Li et al. ............. 378/23 |
| 7,003,146 | B2 | * | 2/2006 | Eck et al. ............ 382/132 |
| 7,110,498 | B2 | * | 9/2006 | Yamada ............... 378/98.8 |
| 7,144,158 | B2 | * | 12/2006 | Dippl et al. .......... 378/177 |
| 7,236,572 | B2 | * | 6/2007 | Maschke ............. 378/146 |
| 2005/0061963 | A1 | | 3/2005 | Spahn et al. |
| 2005/0265523 | A1 | * | 12/2005 | Strobel .............. 378/193 |
| 2006/0116566 | A1 | * | 6/2006 | Bruijns .............. 600/407 |
| 2006/0126797 | A1 | * | 6/2006 | Hoernig .............. 378/207 |

FOREIGN PATENT DOCUMENTS

| DE | 103 03 940 A1 | 8/2004 |
| DE | 103 12 450 A1 | 10/2004 |

* cited by examiner

*Primary Examiner*—Edward J. Glick
*Assistant Examiner*—Thomas R Artman

(57) ABSTRACT

In a method to create a gain-corrected x-ray image with the aid of a flat-panel x-ray detector a number of gain images are determined on calibration and this is done for different measurement situations which correspond to different settings of specific x-ray imaging variables such as the angle of the flat-panel x-ray detector to an x-ray tube, the energy of the x-radiation used etc. Instead of the usual gain image for each element of the detector, a gain value is then used in the gain correction which is produced from an interpolation of the corresponding values from the number of gain images.

9 Claims, 2 Drawing Sheets

# METHOD FOR GENERATING A GAIN-CORRECTED X-RAY IMAGE

CROSS REFERENCE TO RELATED APPLICATIONS

This application claims priority to the German Application No. 10 2005 017 491.4, filed Apr. 15, 2005 which is incorporated by reference herein in its entirety.

FIELD OF INVENTION

The invention relates to a method for generating a gain-corrected x-ray image with the aid of a flat-panel detector in accordance with the preamble of claim 1. Such a method is known from US 2005/00 61 963 A1 and DE 103 12 450 A1.

BACKGROUND OF INVENTION

Flat-panel x-ray detectors are used increasingly frequently in x-ray imaging systems. A flat-panel x-ray detector consists of 1000 by 1000 to around 3000 by 3000 detector elements under a scintillator, such as cesium iodide for example. The x-rays converted into light by the scintillator are measured in the detector elements and converted into a data value which is then represented as a gray-scale value, so that the individual pixels can be assembled into an x-ray image.

A flat-panel x-ray detector can for example be a solid-state x-ray detector made of amorphous silicon. Such a detector has the property that the signal behavior of each individual detector element is different. This means that different areas of the detector have different sensitivities to x-ray radiation. Gain correction is thus undertaken when an x-ray image is generated in which the data values are corrected by purely computational means. The basis for the correction is the previous measurement of the relevant sensitivity of the individual detector elements. This measurement is undertaken by determining a so-called gain image, with the gain image providing a gain value in each image element or pixel. In the prior art a single gain image is determined for calibration of an x-ray imaging system when the system is commissioned. "Determining" a gain image is taken in this case to mean that a gain image is obtained by recording multiple images, and that a gain image is obtained by recording a plurality of bright images, i.e. images, for which the x-ray radiation arrives at the flat-panel x-ray detector in a defined and direct manner, without an imaging object disturbing the path of the x-ray radiation. This plurality of bright images is recorded without any changes to the x-ray imaging settings and a plurality of dark images is then recorded. An average is then taken from the bright images, i.e. an averaged pixel data value is determined over the various images for each individual pixel. The dark images are images which are recorded without x-ray radiation being emitted at all. The dark images correspond to the signals of the detector elements which emit these signals in any event, i.e. to an offset of the signals. This offset is then derived for each detector element from the associated averaged data value for the bright images and a gain image is determined in this manner. As a rule the data value from the gain image is also standardized to 1. An image entry for an individual pixel of 1,1 means for example that the corresponding detector element reflects the x-ray radiation amplified by a factor of 1,1, so that to record an x-ray image, the data value emitted by this detector element must be divided by 1,1, in order to thus obtain a data value which corresponds to a gain of 1. Conversely a gain value of 0.9 means that the detector element is slightly weaker than the average, and that a corresponding data value of an x-ray image must be divided by 0,9 in order to thus obtain a slightly increased data value which corresponds to a realistic data value for an average detector element.

SUMMARY OF INVENTION

The gain-corrected x-ray image obtained in this way is thus an x-ray image in which the individual influence of the individual detector elements is largely excluded.

As already explained above, a single gain image is determined in the prior art in a predetermined position of the detector in relation to the x-ray tube.

The recording of different gain images depending on an image recording size which is used as a parameter for a later interpretation is known in US 2005/00 61 963 A1 and DE 103 12 450 A1.

However with modem x-ray flat-panel detectors there are also geometrical effects. In other words the individual gain value which would have to be assigned to a detector element is not independent of the angular position of the detector in relation to the x-ray tube. What is known as the Heel effect contributes to this. When the x-ray detector is turned areas at the edge of the detector can also be shadowed (dome effect). DE 103 03 940 A1 also deals with this problem.

An object of the invention is thus to better detect the individual deviations of the detector elements from the norm in order to thus be able to improve the quality of the gain correction.

Basically the invention is based on determining more than a single gain image. The method does not just stop at determining only one gain image in a predetermined position of detector to the x-ray tube and with a predetermined x-ray dose and x-radiation wavelength. Instead at least two different gain images are determined depending on an imaging variable. This imaging variable can be the angular position of the flat-panel x-ray image detector in relation to an x-ray tube, the energy of the x-radiation used or also the setting of a filter for filtering out part of a dose from the x-radiation used.

Preferably the gain images are recorded as a function of that imaging variable which is changed the most and the soonest.

The relevant setting relating to the imaging variable is then determined for recording an x-ray image, i.e. electronically assigned a data value and used for a gain correction. Use for gain correction is based on the fact that an interpolation is undertaken. The interpolation is linear in the simplest case but can also be polynomial interpolation. The interpolation is preferably undertaken in real time (e.g. in a 30-Hz clock)

Preferably at least two of the gain images are assigned imaging variables which correspond to limit values of the same, i.e. at which the associated settings are more extreme. The reason for this is that the interpolation is easier to handle if this type of so-called inner interpolation is involved. In other words the settings for a real recorded x-ray image are preferably located between the settings which were used for the determination of the gain images and not outside these settings.

In accordance with the invention the angular setting of the flat-panel x-ray detector of an x-ray tube, viewed in the flat plane of the flat-panel x-ray detector is recorded as the imaging variable or as one of the imaging variables. The two limit values correspond to the inventive values of 0° and 90°. An intermediate value of 45° can still be used for which a gain image is created. The invention does not exclude the combination of interpolation as a function of the angular setting with interpolations relating to the energy of the x-rays used and the setting of a filter for filtering out a part of the dose from the x-radiation used.

BRIEF DESCRIPTION OF THE DRAWINGS

A preferred embodiment of the invention is now described with reference to the drawings, in which.

DETAILED DESCRIPTION OF INVENTION

Figure 1:
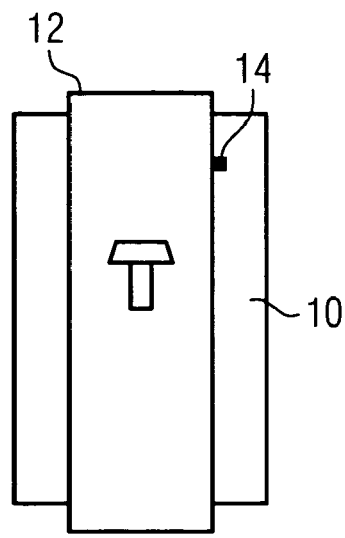
FIG. 1 shows the position of a flat panel x-ray detector in relation to an x-ray tube in a first measurement situation, as well as a schematic diagram of an associated gain image.
Figure 1:
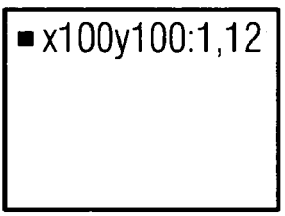
Figure 2:
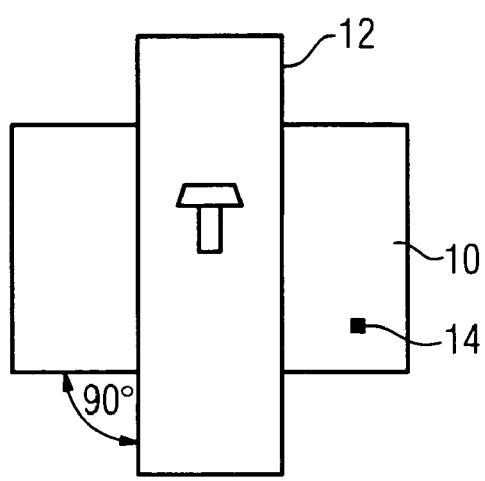
FIG. 2 shows the position of the flat panel x-ray detector in relation to an x-ray tube in a second measurement situation, as well as a schematic diagram of an associated gain image.
Figure 2:
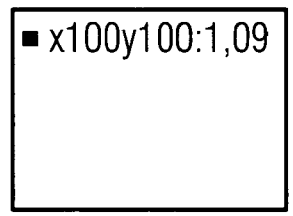
Figure 3:
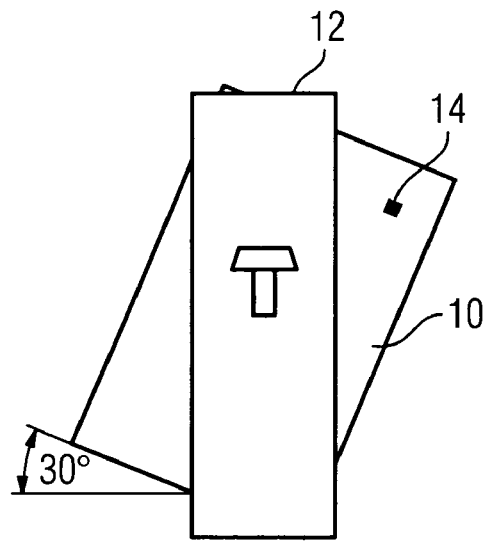
FIG. 3 shows the position of a flat panel x-ray detector in relation to an x-ray tube during a recording of an x-ray image as well as a schematic diagram of a gain image determined for this image by interpolation.
Figure 3:
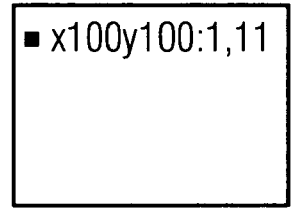

FIGS. 1 to 3 illustrate the recording of various gain images for various angular positions of the flat-panel x-ray detector in relation to the x-ray tube 12.

FIG. 1 illustrates a basic setting in which the flat-panel X-ray detector at 10 is at an angle of 0° in relation to the x-ray tube 12.

To illustrate a gain image recorded in this measurement situation the value for an image element shown here as a rectangle is specified, in this case 1,12. The detector element 14 corresponding to this pixel is shown drawn in in the upper section of FIG. 1.

FIG. 2 now relates to a second measurement situation: A further gain image is recorded for the situation in which the flat-panel x-ray detector at 10 is turned by 90° in relation to the x-ray tube. In the gain image which is indicated schematically in the lower section of FIG. 2, the position of the pixel is the same whereas the real detector element 14 has turned. As a result of geometrical effects the associated gain value does not now amount to 1.12 but only to 1.09.

FIG. 3 now shows a third situation. In this third situation the flat-panel x-ray detector 10 is turned thorough 30° in relation to the x-ray tube 12.

The result of the geometrical effects is that neither the gain value determined in relation to the measurement situation from FIG. 1 nor the gain value determined in relation to the measurement situation from FIG. 2 is the correct value. An approximately real gain value for the detector element 14 involved is obtained by interpolation of the gain values from the two gain images. Since an angle of 30° is twice as close to the position of 0° as to the position of 90° a linear interpolation is produced which, to determine a suitable gain value for the image recording situation shown in FIG. 3, has to multiply the gain value from FIG. 1 by two and the gain value from FIG. 2 by 1, with the total then being divided by 3. Linear interpolation of thus produces a gain value of 1.11 for a rotation by 30°. For a rotation by 60° a corresponding a gain value of 1.10 would be produced. This makes it clear that the interpolation is actually a linear interpolation.

The gain values of 1.12 and 1.09 specified in FIGS. 1 and 2 are determined by measurement whereas the gain value of 1.11 shown in Figure three has exclusively been determined by interpolation.

For a linear interpolation in relation to an angular position it is sufficient to determine two gain images between the extreme settings of the detector. Since the detector is only able to be turned between 0° and 90° it is recommended that a measurement be taken both at 0° and also at 90°. With a slightly improved embodiment a third gain image can be determined at an angle of 45°, but basically two gain images are sufficient.

In a similar manner the image recording variable "wave length of the x-radiation" can be changed. This is predetermined by the voltage present at the x-ray tube, here in kV.

Figure 4:
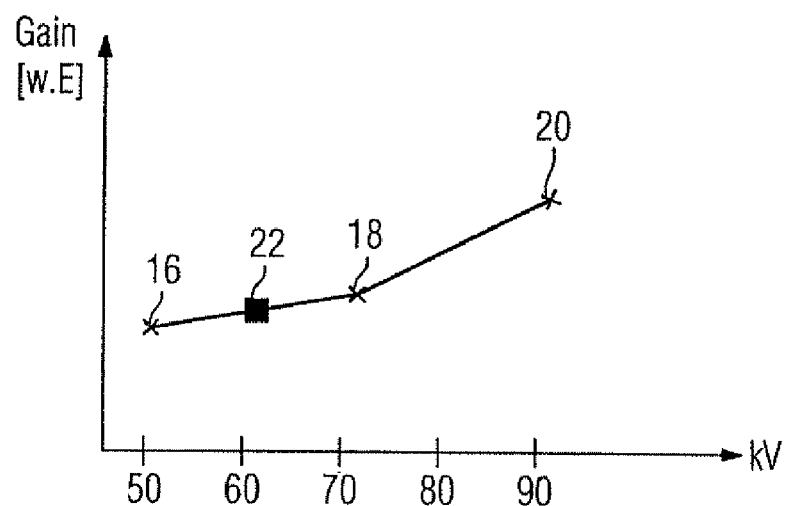
FIG. 4 shows a graph which represents the dependency of the gain on the wavelength of the x-rays.

FIG. 4 shows a graph of measured values relating to a single detector element, with the relevant gain being entered as a function of the acceleration voltage. Three measurement points 16, 18 and 20 are shown. The measured value 16 reflects the gain at an acceleration voltage of 50 kV, the measured value 18 at an acceleration voltage of 70 kV and the measured value 20 at an acceleration voltage of 90 kV. Arbitrary units for the gain are shown here, which are known to be standardized to 1 in any event.

A predetermined situation will now be examined in which a specific x-ray image is recorded at an acceleration voltage of 61 kV.

Advantageously a value is produced for the associated gain for the detector element referred to here by linear interpolation from the measured values 16 and 18. The interpolation value 22 (shown as a square symbol) is indicated on the graph. Alternately a polynomial interpolation would also be possible in which the measured value 20 could also be taken into account.

Figure 5:
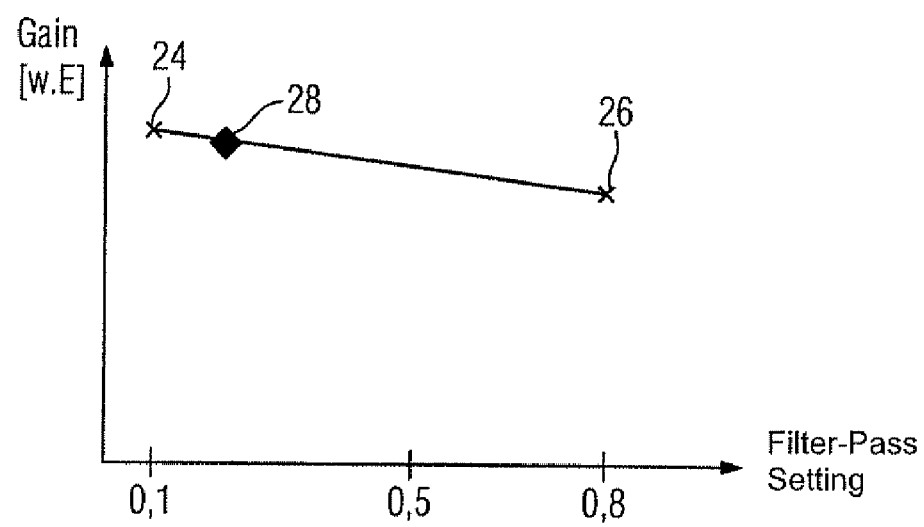
FIG. 5 shows a graph which shows the dependence of the gain on the setting of a filter.

FIG. 5 is based on the fact that the gain can also depend on the setting of a copper filter, which determines the dose of x-ray power. The gain is thus dose-dependent. Shown in the diagram are a measuring point 24 for a setting in which the filter lets through 0.1 proportions of the x-radiation and a measuring point in which the filter lets through 0.8 proportions of the x-radiation. If an x-ray image is now recorded at a filter setting relating to the filtration in which the lets through 0.2 proportions of x-radiation, the intermediate value 28 shown in the diagram in the shape of a diamond is now used to obtain an interpolated gain value. This is undertaken detector element-by-detector element, that is pixel-by-pixel corresponding to the gain images present for pixels 24 and 26, so that a interpolated gain image is obtained belonging to the filtration of 0,2 corresponding to the points 28 per detector element.

It has previously been shown that at least two gain images can be recorded in each case for different angular settings of the flat-panel x-ray detector in relation to the x-ray tube, different acceleration voltages and different filter settings. These can also be basically combined with each other. For example the gain values shown in FIG. 4 corresponding to the pixels 16 and 20 are taken at an angular setting of 0°. An additional measurement can then be undertaken at a 90° angular setting, for which for the two given values of 50 and 90 kV acceleration voltage a gain image is also determined, so that overall four gain images are available and can be interpolated two-dimensionally, that is depending on two parameters.

The interpolation can be improved by knowledge of the causes of the changing gain values, for example specific formulae can be fitted for interpolation etc.

The invention claimed is:

1. A method of generating a gain-corrected x-ray image using a flat-panel x-ray detector having a plurality of detector elements, the method comprising:

a calibration step comprising determining a plurality of gain images for a plurality of different imaging variables settings, the different imaging variables settings related to at least one imaging variable, each gain image having a plurality of gain values each gain value corresponding to one of the plurality of detector elements;

an x-ray recording step comprising determining a current imaging variables setting of the imaging variable and assigning a data value to each of at least part of the detector elements based on the current imaging variables setting; and a correcting step comprising a gain correction of the assigned data values using at least two of the gain images, the gain correction including correcting each data value based upon an interpolation between corresponding pixels of the at least two of the gain images, the interpolation executed with regard to the current imaging variables setting of the imaging variable, wherein the imaging variable includes a rotation angle of the flat-panel x-ray detector relative to an x-ray tube, the rotation angle representing a rotation of a flat plane in which the flat-panel x-ray detector is arranged relative to a position about which the x-ray tube is arranged, and the plurality of gain images include gain images for imaging variables settings of the rotation angle being 0° and 90°, wherein the imaging variable further includes a filter setting for a filter configured to filter out part of an x-ray dose of the x-ray tube.

2. The method in accordance with claim 1, wherein the plurality of gain images further include a gain image for an imaging variables settings of the rotation angle being 45°.

3. The method in accordance with claim 1, wherein the imaging variable further includes an energy of x-rays used for recording the gain images or the x-ray.

4. The method in accordance with claim 1, wherein the interpolation includes a linear interpolation based on the rotation angle.

5. The method in accordance with claim 1, wherein the interpolation includes a polynomial interpolation.

6. An x-ray imaging system, comprising:

a flat-panel x-ray detector having a plurality of detector elements for recording a plurality of data values, and an image processing unit configured to:

generate and store a plurality of gain images for a plurality of different imaging variable settings, each of the settings related to at least one imaging variable, each gain image having a plurality of gain values with each gain value corresponding to one of the plurality of detector elements; and generate at least part of the data values based on gain values included in the gain images, wherein each gain value is derived from an interpolation between corresponding pixels of at least two of the gain images, wherein the imaging variable includes a rotation angle of the flat-panel x-ray detector relative to an x-ray tube, the rotation angle representing a rotation of a flat plane in which the flat-panel x-ray detector is arranged relative to a position about which the x-ray tube is arranged, and the plurality of gain images include gain images for imaging variable settings of at least two rotation angles, wherein the imaging variable further includes a filter setting for a filter configured to filter out part of an x-ray dose of the x-ray tube.

7. The An x-ray imaging system in accordance with claim 6, wherein the interpolation is executed by the image processing unit in real time while recording an x-ray image.

8. The x-ray imaging system in accordance with claim 6, wherein the interpolation is executed by the image processing unit relative to an imaging variable.

9. The x-ray imaging system in accordance with claim 8, wherein a setting of the imaging variable is automatically fed to the image processing unit when an x-ray image is recorded.

* * * * *